US00RE34299E

United States Patent [19]

Perregaard

[11] E Patent Number: Re. 34,299

[45] Reissued Date of Patent: Jun. 29, 1993

[54] 1-(4'-FLUOROPHENYL)-3,5-SUBSTITUTED INDOLES USEFUL IN THE TREATMENT OF PSYCHIC DISORDERS AND PHARMACEUTICAL COMPOSITIONS THEREOF

[75] Inventor: Jens K. Perregaard, Jaegerspris, Denmark

[73] Assignee: H. Lundbeck A/S, Copenhagen-Valby, Denmark

[21] Appl. No.: 759,517

[22] Filed: Sep. 13, 1991

Related U.S. Patent Documents

Reissue of:

[64] Patent No.: 4,710,500
Issued: Dec. 1, 1987
Appl. No.: 846,912
Filed: Apr. 1, 1986

[30] Foreign Application Priority Data

Apr. 10, 1985 [GB] United Kingdom ..... 8509164

[51] Int. Cl.[5] ..... A61K 31/495; A61K 31/435; A61K 31/44; C07D 403/04; C07D 401.06; C07D 209/04

[52] U.S. Cl. ..... 514/254; 514/226.8; 514/227.2; 514/228.8; 514/252; 514/253; 514/323; 514/333; 514/339; 544/54; 544/55; 544/96; 544/97; 544/295; 544/333; 544/364; 544/369; 544/370; 544/373; 546/188; 546/193; 546/201; 546/256; 546/273

[58] Field of Search ..... 544/54, 55, 96, 97, 544/295, 233, 370, 373, 364, 369, 54, 55, 96, 97, 295, 333; 546/188, 193, 201, 273, 256; 514/253, 254, 339, 252, 323, 333, 226.8, 227.2, 228.8

[56] References Cited

U.S. PATENT DOCUMENTS 3,429,886 2/1969 Beck et al. ..... 544/373
3,850,938 11/1974 Derible et al. ..... 546/273

(List continued on next page.)

FOREIGN PATENT DOCUMENTS 0003199 7/1979 European Pat. Off. .
0003200 7/1979 European Pat. Off. .
0022705 1/1981 European Pat. Off. .
0112191 6/1984 European Pat. Off. .
2811031 9/1978 Fed. Rep. of Germany .
2178027 11/1973 France .
2227873 11/1974 France .
2458550 6/1979 France .
1570374 7/1980 United Kingdom .

OTHER PUBLICATIONS

Buzas et al., CA 90-38962m.
Buzas et al., CA 93-8014y.
Guillaume et al., CA 94-156767g.

*Primary Examiner*—Cecilia Tsang
*Attorney, Agent, or Firm*—Dressler, Goldsmith, Shore, Sutker & Milnamow, Ltd.

[57] ABSTRACT

The present invention relates to novel indole derivatives which have interesting pharmacodynamic effects indicating pronounced activity in the treatment of psychic disorders, especially psychoses and, at the same time, a low degree of undesired side effects.

Moreover, the invention relates to methods for the preparation of said indole derivatives, pharmaceutical compositions containing same, and methods for the treatment of psychic disorders, especially psychoses, by administering a therapeutically active amount of one of said derivatives to a living animal body, including human beings.

The novel indole derivatives of the present invention are represented by the following formula;

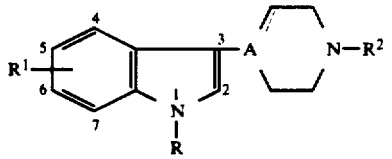

wherein R is phenyl, optionally substituted with halogen[, lower alkyl or trifluoromethyl,] or a hetero aromatic group, such as 2-thienyl, 3-thienyl, [2-furoyl, 3-furoyl, 2-thiazol, 2-oxazol, 2-imidazole, 2-pyridyl, 3-pyridyl] *2-oxazolyl, 2-imidazolyl, 2-pyridyl 3-pyridyl*or 4-pyridyl; $R^1$ is hydrogen, halogen, lower alkyl, lower alkoxy, hydroxy, cyano, nitro, lower alkylthio, trifluoromethyl, lower alkylsulfonyl, amino, lower alkylamino or lower di-alkylamino; "A" is nitrogen or carbon, and the dotted line indicates—when A is carbon—an optional bond; $R^2$ is hydrogen, cycloalkyl, lower alkyl or lower alkenyl, optionally substituted with one or two hydroxy groups, any hydroxy group present being optionally esterified with an aliphatic carboxylic acid radical having from two to twenty-four carbon atoms inclusive, or $R^2$ is the group

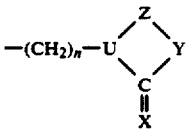

wherein "n" is an integer of 2-6; X is oxygen or sulfur, or <C=X may constitute the group [>] =CH= when Y is =N— or =CH—; Y is oxygen, sulfur, $CH_2$ or N $R^3$, where $R^3$ is hydrogen, [or] lower alkyl, lower alkenyl or a cycloalkylmethyl group, said "cycloalkyl" having from three to six carbon atoms inclusive; Z is $—(CH_2)_m—$, "m" being 2 or 3, or Z is —CH=-CH— or 1,2-phenylene optionally substituted with halogen or trifluoromethyl, or Z is —CO(or S)$CH_2$—; U is nitrogen or carbon provided that when $R^1$ is *hydrogen,* chloro, *lower alkyl, methoxy or hydroxy,* A is nitrogen and $R^2$ is [methyl or cyclohexyl] *lower alky or cycloalkyl of* $C_3$—$C_6$, R may not be phenyl; as well as their pharmaceutically acceptable acid addition salts.

9 Claims, No Drawings

U.S. PATENT DOCUMENTS

| | | | |
|---|---|---|---|
| 3,947,578 | 3/1976 | Derible et al. | 546/273 |
| 3,980,658 | 9/1976 | Possanza et al. | 546/273 |
| 3,993,764 | 11/1976 | Dumont et al. | 546/273 |
| 4,100,291 | 7/1978 | Clemence et al. | 546/273 |
| 4,195,081 | 3/1980 | Nedelec et al. | 546/273 |
| 4,196,209 | 4/1980 | Dumont et al. | 546/273 |
| 4,232,031 | 11/1980 | Dumont et al. | 546/273 |
| 4,278,677 | 7/1981 | Nedelec et al. | 546/273 |
| 4,324,790 | 4/1982 | Guillaume et al. | 546/273 |
| 4,333,939 | 6/1982 | Guillaume et al. | 546/273 |
| 4,352,811 | 10/1982 | Strupczewski et al. | 546/198 |
| 4,359,468 | 11/1982 | Freter et al. | 546/199 |
| 4,443,448 | 4/1984 | Bøgesø | 544/369 |
| 4,458,076 | 7/1984 | Strupczewski | 544/199 |
| 4,524,074 | 6/1985 | Strupczewski | 514/321 |
| 4,525,360 | 6/1985 | Perregaard | 514/277 |
| 4,530,932 | 7/1985 | Clemence et al. | 546/273 |
| 4,670,447 | 6/1987 | Strupczewski | 514/322 |
| 4,684,650 | 8/1987 | Bøgesø | 514/252 |
| 4,710,573 | 12/1987 | Strupczewski | 546/199 |
| 4,758,668 | 7/1988 | Strupczewski | 546/199 |
| 4,775,761 | 10/1988 | Strupczewski | 546/199 |
| 4,806,649 | 2/1989 | Strupczewski | 546/193 |
| 4,853,470 | 8/1989 | Strupczewski | 546/199 |

1-(4'-FLUOROPHENYL)-3,5-SUBSTITUTED INDOLES USEFUL IN THE TREATMENT OF PSYCHIC DISORDERS AND PHARMACEUTICAL COMPOSITIONS THEREOF

Matter enclosed in heavy brackets [ ] appears in the original patent but forms no part of this reissue specification; matter printed in italics indicates the additions made by reissue.

BACKGROUND OF THE INVENTION

In the past, several indole derivatives being substituted at the nitrogen atom with a carboxylic acid radical have been found to possess [analgetic] *analgesic* and antiinflammatory properties. Recently it was suggested in German OLS No. 2811031 that also indoles having a phenylsubstituent at the nitrogen atom might have the desired [analgetic] *analgesic* or antiinflammatory effects, but no data were given for the [1-phenyl-5-chloro-3-methylpiperanzineindole *1-phenyl-5-chloro-3-(4-methyl-1-piperazinyl)-1-phenylindole or* 1-phenyl-5-chloro-3-cyclohexyl-piperazineimdole actually disclosed in the specification. We have prepared the first-mentioned of these compound Lu23-015) and found that it was without interesting effects *as compared to the closest related compound of the invention, i.e., 5-chloro-1-(4-*fluorophenyl)*-3-(4-methyl-1-piperazinyl)indole (Lu 23-011)*, in the pharmacological testing carried out in our laboratories.

In European Patent application No. 80401005.6 some derivatives of tetrahydro-pyridinyl-indoles having at the 1-position either hydrogen or alkyl (1–3 C-atoms), were described as being neuroleptics. The pharmacological data given in the specification, however, indicate only weak to moderate neuroleptic activity.

We have prepared one of these compounds, [5-chloro-3-(1-(2-hydroxyethyl)-1,2,3,6-tetrahydropyrid-4-yl)indol] *5-chloro-3-(1-(2-hydroxyethyl)-1,2,3,6-*tetrahydropyrid-*4-yl)indole* (Lu 23-143) and found that it was almost active compared with the compounds of Formula I.

It has now surprisingly been found that the novel indole derivatives of Formula I are potent dopaminergic antagonists in pharmacological tests[, both in vivo and] in vitro[,] *and many of them also in vivo,* as compared with well-known neuroleptics commonly used in the treatment of psychoses; and especially very long-lasting effects — up to several days — were observed with many of the compounds of Formula I. Additionally, most of the [the] indoles of Formula I are strong 5-HT antogonists both [periferically] *peripherally* and centrally, which is considered to be important for the treatment of psychic disorders or cardiovascular diseases.

The terms lower alkyl, lower alkoxy, lower alkylthio and lower alkysulfonyl designate such groups having from one to four carbon atoms inclusive. Exemplary of such groups are methyl, ethyl, n-propyl, iso-propyl, n-butyl, sec.butyl, methoxy, ethoxy, propoxy, butoxy, methylthio, ethylthio, propylthio, methylsulfonyl, ethylsulfonyl, or the like.

The term lower alkenyl designates alkenyl groups having from two to four carbon atoms, for example ethenyl, 1-propenyl, 2-butenyl, or the like.

This invention also includes pharmaceutically acceptable salts of the compounds of Formula I formed with non-toxic acids. Such salts are easily prepared by methods known to the art.

The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly.

Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids. Of course, these salts may also be prepared by the classical method of double decomposition of appropriate salts, which is well-known to the art.

The compounds of Formula I as well as the pharmaceutically acceptable acid addition salts thereof may be administered both orally and parenterally, for example in the form of tablets, capsules, powders, syrups or solutions for injection.

Of the indoles of Formula I, those wherein $R^1$ is chlorine, fluorine, trifluoromethyl, methyl, nitro or amino in the 5-position, R is phenyl substituted with fluroine in the 4'-or the 2'-position, $R^2$ is methyl, hydroxyethyl or 3-hydroxypropyl, and A is as defined above, have shown especially favourable effects in the pharmacological testing, and also have few undesired side effects.

The invention moreover relates to a method for the preparation of the novel indoles of Formula I, which comprises (a) reacting an indole derivative of the following formula:

II

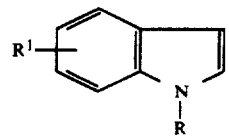

wherein $R^1$ and R are as defined above, with a 4-piperidone of the formula:

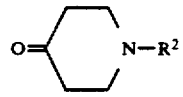

wherein $R^2$ is as defined above, or (b) reducing a compound of the following formula:

III

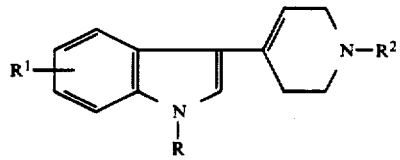

wherein $R^1$, R and $R^2$ are as defined above, or (c) reacting a compound of the following formula:

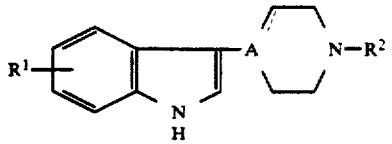

IV wherein $R^1$, $R^2$ and A are defined above, with a compound of formula:

wherein R is as defined above and "hal" is halogen, in the presence of a metal catalyst, or (d) reacting a compound of the following formula:

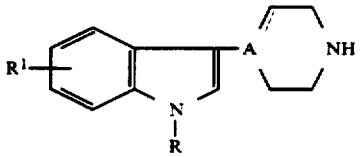

V wherein $R^1$, R and A are as defined above, with a lower alkyl halide or an epoxide of formula

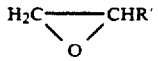

wherein [R] *R'* is hydrogen, methyl or ethyl, or (e) reducing a compound of the following formula:

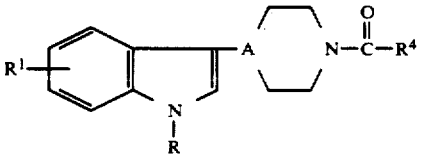

VI wherein $R^1$, R and A are as defined above and $R^4$ is hydrogen, lower alkyl (1-3 C-atoms) or lower alkoxy (1-3 C-atoms), or (f) heating a compound of the following formula:

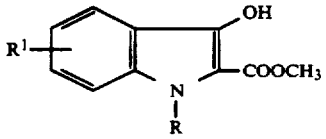

VII wherein $R^1$ and R *are* as defined above, with a piperazine of formula:

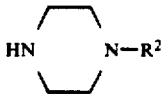

wherein $R^2$ is as defined above, or (g) reducing a compound of the following formula:

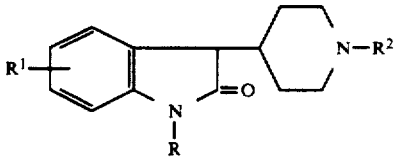

VIII wherein $R^1$, R and $R^2$ are as defined above, with a suitable reducing agent, whereupon the indole of Formula I is isolated in the form of the free base or a pharmaceutically acceptable acid addition salt thereof, and if the group $R^2$ contains one or two hydroxyl groups, if desired, acylating such a hydroxy group with a reactive derivative of an aliphatic carboxylic acid having from two to twenty-four carbon atoms, and isolating the ester formed as the free base or a pharmaceutically acceptable acid addition salt thereof.

In method (a) the reaction is performed under strong acidic conditions by heating. Trifluoroacetic acid or HCl in ethanol are preferred as acid catalysts. The starting compounds of Formula II are conveniently prepared according to procedures described in the literature, e.g. by reduction of R substituted isatins or oxindoles by a method described by H. Sirowej et al, in Synthesis 1972, 84, according to the following reaction scheme:

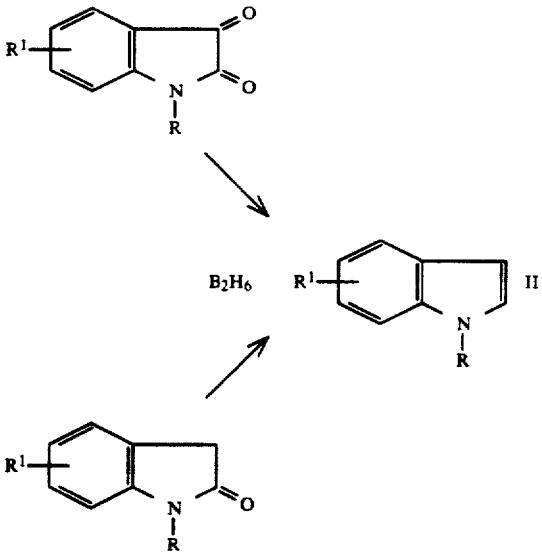

Isatins and oxindoles are prepared by a [Fiedel-Craft] *Friedel-Craft* ring closure under standard conditions from N-oxalylchloro-or N-(2-chloroacetyl) diphenylamines respectively. The compounds of Formula II may alternatively be prepared by arylation of N-unsubstituted indoles according to the method described by M.A. Khan and E.K. Rocha, Chem.Pharm.Bull. 25 (11), 3110-3114 (1977).

An alternative way of obtaining the intermediates of Formula II is that from an indoxyl-2-carboxylic ester as outlined below:

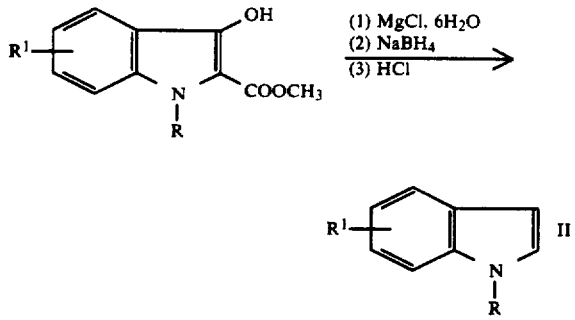

in method (b) the reduction is preferably carried out at low hydrogen pressures (3 ato.) in the presence of platinum or palladium on carbon black.

In method (c) the arylation is preferably carried out at about 160°-210° C. in aprotic polar solvents as e.g. N-methyl-2-pyrrolidone or hexamethylphosphoric triamide with $K_2CO_3$ as base and copper as a catalyst. In method (e) the reduction is preferably carried out with $LiAlH_4$ in THF or diethylether or with diborane in THF.

Method (f) is a two step procedure in which compound VII first is decarboxyalkylated in the presence of an inorganic salt as e.g. LiCl or $MgCl_2$ in a polar solvent as e.g. diglyme, hexamethylphosphoric triameide or N-methyl-2-pyrrolidone at elevated temperatures (120°-150° C.). Finally, the appropriate piperazine is added and the temperature raised to about 200° C. and kept there until the corresponding indoxyle has disappeared according to TLC analysis. The compounds of Formula VII are conveniently prepared according to the procedures reported by P. C. Unangst and M. E. Carethers, J.Heterocyclic Chem. 21, 709 (1984).

In method (g) diborane in THF is conveniently used as a reducing agent. The compounds of Formula VIII are prepared from the corresponding R-substituted isatins according to the following reaction scheme:

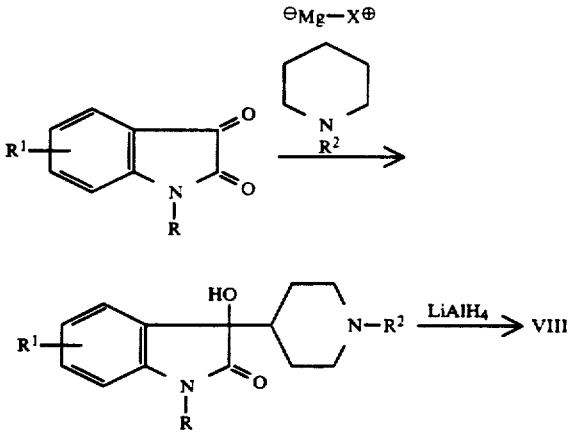

The methods of the invention shall be illustrated in the following by some examples, which may not be construed as limiting:

EXAMPLE 1

(Method a)

1-(4'-Fluorophenyl)-5-methyl-3-(1-methyl-1,2,3,6-tetrahydropyridin-4-yl)-1H-indole, hydrochloride (Lu 20-089).

1-(4'-fluorophenyl)-5-methyl-1H-indole (4.5 g) and 1-methyl-4-piperidone (5 g) were dissolved in 25 ml of acetic acid and added dropwise to 50 ml of trifluoroacetic acid kept almost at the boiling point. The mixture was gently refluxed for another ½ h. Excess trifluoroacetic acid was evaporated and the reaction mixture was added to 50 ml of 6 M HCl and 50 ml of ether. The precipitated title compound was filtered off and dried. Yield: 3.1 g (43%). M.p. 262°-266° C.

In a corresponding manner the following tretrahydropyridin-4-ylindoes were prepared:

5-Fluoro-1-(4'-fluorophenyl)-3-(1-methyl-1,2,3,6-tetrahydropyridin-4-yl)-1H-indole, hydrochloride. (Lu 21-018). M.p. 256° C.

1-(4'-Fluorophenyl)-3-(1-methyl-1,2,3,6-tetrahydropyridin-4-yl)-5-trifluoromethyl-1H-indole, oxalate. (Lu 21-120). M.p. 228°-229° C.

1-(4'-Fluorophenyl)-5-nitro-3-(1-methyl-1,2,3,6-tetrahydropyridin-4yl)-1H-indole. (Lu 22-135). M.p. 168°-170° C.

1-(3'-Fluorophenyl)-5-nitro-3-(1-methyl-1,2,3,6-tetrahydropyridin-4-yl)-1H-indole, maleate. (Lu 24-004). M.p. 216°-217° C.

1-(2'-Fluorophenyl)-5-nitro-3-(1-methyl-1,2,3,6-tetrahydropyridin-4-yl)-1H-indole, maleate. (Lu 24-003). M.p. 208° C.

3-(1-(2-Hydroxyethyl)-1,2,3,6-tetrahydropyridin-4-yl)-1-(4'-trifluoromethylphenyl)-1H-indole, fumarate. (Lu 24-012). M.p. 174°-175° C.

1-(4'-Fluorophenyl)-3-(1-methyl-1,2,3,6-tetrahydropyridin-4-yl)-1H-indole, hydrochloride. (Lu 23-083). M.p. 268°-270° C.

1-(4'-Fluorophenyl)-5-nitro-3-(1,2,3,6-tetrahydropyridin-4-yl)-1H-indole, maleate. (Lu 23-133). M.p. 204°-205° C.

5-Chloro-1-(4'-fluorophenyl)-3-(1-(2-hydroxyethyl)-1,2,3,6tetrahydropyridin -4yl)-1H indole, hydrochloride. (Lu 23-146). M.p. 280°-282° C.

5-Chloro-1-(4'-fluorophenyl)-3-(1,2,3,6-tetrahydropyridin-4-yl)-1H-indole. (Lu 23-147). M.p. 105° C.

1-(4'-fluorophenyl)-3-(1-(2-hydroxyethyl)-1,2,3,6-tetrahydropyridin-4-yl)-5-nitro-1H-indole. (Lu 23-150). M.p. 151°-152° C.

1-(4'-Fluorophenyl)-3-(1,2,3,6-tetrahydropyridin-4-yl)-5-trifluoromethyl-1H-indole. (Lu 23-155). M.p. 128°-130° C.

1-(4'-Fluorophenyl)-3-1-(2-hydroxyethyl-1,2,3,6-tetrahydropyridin-4-yl)-5-trifluoromethyl-1H-indole. (Lu 23-156). M.p. 140°-141° C.

5-fluoro-1-(4'-fluorophenyl)-3-(1,2,3,6-tetrahydropyridin-4-yl)-1H-indole. (Lu 23-159). M.p. 75°-77° C.

5-fluoro-1-(4'-fluorophenyl)-3-(1-(2-hydroxyethyl)-1,2,3,6-tetrahydropyridin-4-yl)-1H-indole, oxalate. (Lu 23-160). M.p. 180°-184° C.

5-fluoro-1-(4'-fluorophenyl)-3-(1-(2-propyl-1,2,3,6-tetrahydropyridin-4-yl)-1H-indole, fumarate. (Lu 23-167). M.p. 190°-195° C.

1-(4'-Fluorophenyl)-3-(1-(3-hydroxypropyl)-1,2,3,6-tetrahydropyridin-4-yl)-5trifluoromethyl-1H-indole. (Lu 23-171). M.p. 159°-161° C.

5-Fluoro-1-(4'-fluorophenyl)-3-(1-(3-hydroxypropyl-1,2,3,6-tetrahydropyridin-4-yl)-1H-indole, oxalate. (Lu 23-175). M.p. 173°-175° C.

EXAMPLE 2

(method b)

1-(4'-Fluorophenyl)-3-(1-methyl-4-piperidyl)-5-trifluoromethyl-1H-indole, oxalate. (Lu 21-131).

Compound Lu 21-120, oxalate (2.5 g) is dissloved in ethanol (200 ml), and $PtO_2$(0.2 g) is added. Hydrogenation is continued for 3h at 3 atm. The catalyst was then filtered off, ethanol evaporated and the title compound crystallized from acetone/ether. Yield: 1.2 g (48%). M.p. 251°-252° C.

In a corresponding manner were also prepared:

[1-(4'-Fluorophenyl)-3-(1-(2-imidazolidinon-1-yl)ethyl)-4-piperidyl)-1H-indole.]

*1-(4'-Fluorophenyl)-3-(1-(2-(2-imidazolidinon-1-yl)ethyl)-4-piperidyl)-1H-indole.* (Lu 23-086). M.p. 174°-175° C.

[1-(4'-Fluorophenyl)-3-(1-(1-pyrrolidinon-2-onylethyl-4-piperidyl)-5-trifluoromethyl-1H-indole, fumarate.]

*1-(4'-Fluorophenyl)-3-(1-(2-(1-pyrrolidinon-2-onyl)ethyl)-4-piperidyl)-5-trifluoromethyl-1H-indole, fumarate. (Lu* 23-158). M.p. 240°-241° C.

[5-Chloro-1-(4'-fluorophenyl)-3-(1-(2-imidazolidinon-1-ylethyl)-4-piperidyl)-1H-indole, maleate.]

*5-Chloro-1-(4'-fluorophenyl)-3-(1-(2-(2imidazolidinon-1-yl)ethyl)-4-piperidyl)-1H-indole,* maleate.(Lu 23-174). M.p. 155°-160° C.

EXAMPLE 3

(Method c)

3-(1-Methyl-1,2,3,6-tetrahydropyridin-4-yl)-5-nitro-1-pyridin-3-yl-1H-indole. (Lu 24-016).

3-(1-Methyl-1,2,3,6-tetrahydropyridin-4-yl)-5-nitro-1H-indole (4.5 g), 3-bromopyridin (6.0 g), CuBr (4.5 g) and $K_2CO_3$ (8.0 g) *in N-methyl-2-pyrrolidone (25 ml)* were heated under stirring at 160° C. for 2.5 h. After cooling the reaction mixture was poured into diluted $NH_4OH$ (500 ml) and extracted with ethyl acetate (3×300 ml). The combined organic phases were dried ($MgSO_4$) and the solvent evaporated. The title compound was obtained by recrystallization from acetone. Yield: 3.4 g (58%). M.p. 175°-177° C.

In a corresponding manner were also prepared:

3-(1-Methyl-1,2,3,6-tetrahydropyridin-4-yl)-5-nitro-1-pyridin-2-yl-1H-indole. (Lu24-015). M.p. 134° C.

[3-(1-Methyl-1,2,3,6-tetrahydropyridin-4-yl)-5-nitro-1-(2-thiazolo-1H-indole.

*3-(Methyl-1,2,3,6-tetrahydropyridin-4-yl)-5-nitro-1-(2-thiazolyl)-1H-indole.* (Lu 24-022). M.p. 204°-206° C.

5-Chloro-3-(1-methyl-1,2,3,6-tetrahydropyridin-4-yl)-1-(3-thienyl)-1H-indole, maleate. (Lu 24-001). M.p. 168°-170° C.

3-(1-Methyl-1,2,3,6-tetrahydropyridin-4-yl)-5-nitro-1-(2-thienyl)-1H-indole, maleate. Lu 24-014). M.p. 206°-208° C.

EXAMPLE 4

(methods c and e)

5-Chloro-1-(4'-fluorophenyl)-1-methyl-1,2,3,6-tetrahydropyridin-4-yl)-1H-indole, hydrobromide. (Lu 22-117).

5-Chloro-3-(1-carbethoxy-1,2,3,6-tetrahydropyridin-4-yl)-1H-indole (10 g), 1,4-fluoroiodobenzene (15 g), CuBr (10 g) and $K_2CO_3$(15 g) in HMPA (50 ml) were heated (180°-200° C.) while stirring for 3h. After cooling the reaction mixture was poured into $H_2O$ (1 ltr.) and ethylenediamine (100 ml). The crude product was obtained by extraction twice with ether/ethyl acetate (2:1). The combined organic phases were dried [($MgSo_4$)] ($MgSO_4$) and the solvents were evaporated. The pure 5-chloro-1-(4'-fluorophenyl)-3-(1-carbethoxy-1,2,3,6-tetrahydropyridin-4-yl)-1H-indole was obtained by column chromatography on silica gel (eluent 30% ether in dichloromethane). Yield: 8.9 g (68%). M.p. 120°-122° C. The carbethoxy compound [then] *thus* obtained (3 g) was dissolved in dry THF (50 ml) and $LiAlH_4$ pellets (2 g) were added. The mixture was refluxed for 1h, cooled and $H_2O$/THF added to destroy excess $LiAlH_4$. The precipitate was filtered off and THF evaporated. The remaining oil was dissolved in acetone and the title compound precipitated as a hydrobromide salt. Yield: 2.4 g (75%). M.p. 258° C.

In a corresponding manner were also prepared:

5Chloro-1-(4'-fluorophenyl)-3-(1-isobutyl-1,2,3,6-tetrahydropyridin-4yl)-1H-indole, hydrobromide. (Lu 22-134). M.p. 285°-286° C.

[5-Fluro-3-(1-methyl-1,2,3,6-tetrahydropyridin-4-yl)-1-(2-thiazolo)-1H-indole,]

*5-Fluoro-3-(1-methyl-1,2,3,6-tetrahydropyridin-4-yl)-1-(2-thiazoloyl)-1H-indole,* fumarate. (Lu 24-013). M.p. 190°-194° C.

EXAMPLE 5

(method d)

[5-Fluoro-2-(4'-fluorophenyl)-3-(1-(2-imidazolidinon-1-ylethyl)-1,2,3,6-tetrahydropyridin-4-yl)-1H-indole,]

*5-Fluoro-1-(4'-fluorophenyl)-3-(1-(2-(2-imidazolidinon-1yl)ethyl)-1,2,3,6-tetrahydropyridin-4-yl)-1H-indole,* oxalate. (Lu 21-046)

5-Fluoro-1-(4'-fluorophenyl)-3-(1,2,3,6-tetrahydropyridin-4-yl)-1H-indole (2g) prepared as described in Example 1; [1chloroethyl-2-imidazolidinon] *1-(2-chloroethyl)-2-imidazolidinone* (2 g), $K_2CO_3$ (3 g) and a small crystal of KI were refluxed in methyl [isobytyl] *isobutyl* ketone (50 ml) for 16 h. The reaction mixture was poured into $H_2O$ and $CH_2Cl_2$(200 ml) was added. The organic phase was separated, dried ($MgSO_4$) and the solvents evaporated. The crude product was dissolved in acetone and precipitated as an oxalate salt. Yield: 1.2 g (36%) . M.p. 186°-189° C.

In a corresponding manner the following indoles were prepared:

[1-(4'-Fluorophenyl)-3-(4-(2-imidazolidinon-1-ylethyl)-1-piperazino-5-trifluoromethyl-1H-indole,]

*1-(4'-Fluorophenyl)-3-(2-(2-imidazolidinon-1-yl)ethyl-1-piperazinyl)-5-trifluoromethyl-1H-indole,* dihydrobromide. (Lu 23-001). M.p. 262°-263° C.

[1-(4'-Fluorophenyl)-3-(4-(1-pyrrolidin-2-onylethyl)-1-piperazino-5-trifluoromethyl-1H-indole.]

*1-(4'-Fluorophenyl)-3-(4-(2-(1-pyrrolidin-2-onyl)ethyl)-1-piperazinyl)-5-trifluoromethyl-1H-indole.* (Lu 22-133). M.p. 224°-227° C.

[1-(4'-Fluorophenyl)-5-nitro-3-(1-pyrrolidin-2-onlyethyl)-1,2,3,6-tetrahydropyridin-4yl)-1H indole,]

*1-(4'-Fluorophenyl-5-nitro-3-(4-(2-(1-pyrrolidin-2-onyl)ethyl)-1,2,3,6-tetrahydropyridin-4-yl)-1H-indole, hydrochloride. (Lu* 23-024). M.p. 263°-265° C.

[1(4'-Fluorophenyl)-3-(1-(2-imidazolidinon-1-ylethyl)-1,2,3,6-tetrahydropyridin-4-yl)-1H-indole,]

*1-(4'-Fluorophenyl)-3-(1-(2-imidazolidinon-1-*yl)*ethyl)-1,2,3,6-tetrahydropyridin-4-*yl)*-1H-indole,* hydrochloride. (Lu 23-075). M.p. 259°-262° C.

[1-(4'-Fluorophenyl)-5-nitro-3-(1-(2-oxazolidinon-3-ylethyl)-1,2,36-tetrahydropyridin-4yl)-1H-indole,]

*1-(4'-Fluorophenyl)-5-nitro-3-(2(2-(oxazolidinon-3-*yl)*ethyl)-1,2,3,6-*tetrahydropyridin-*4-yl)-1H-indole,* maleate. (Lu 23-134). M.p. 128°-130° C.

[1-(4'-Fluorophenyl)-3-(1-(2-imidazolidinon-1-ylethyl)-1,2,3,6-tetrahydropyridin-4-yl)-5-nitro-1H-indole.]

*1-(4'-Fluorophenyl)-3-(1-(2-(2-imidazolidinon-1-*yl)*ethyl)-1,2,3,6-tetrahydropyridin-4-yl)-5-*nitro-*1H-indole,*(Lu 23-142). M.p. 177°-179° C.

[5-Chloro-1-(4'-fluorophenyl)-3-(1-(2-imidazolidinon-1-ylethyl)-1,2,3,6-tetrahydropyridin-4-yl)-1H-indole.]

*5-Chloro-1-(4'-fluorophenyl)-3-(1-(2-(2-imidazolidinon-1-*yl)*ethyl)-1,2,3,6-*tetrahydropyridin-*4-yl)-1H-indole.* (Lu 23-148). M.p. 138°-140° C.

[1-(4'-Fluorophenyl)-3-(1-(2-imidazolidinon-1-ylethyl)-1,2,3,6-tetrahydropyridin-4-yl)-5-trifluoromethyl-1H-indole.]

*1-(4'-Fluorophenyl)-(1-(2-(2-imidazolidinon-1-*yl)*ethyl)-1,2,3,6-tetrahydropyridin-4-yl)-5-*trifluoromethyl-*1H-indole.* (Lu 23-157). M.p. 164°-165° C.

[1-(2'-Fluorophenyl)-3)-(1-(2-imidazolidinon-1-ylethyl)-1,2,3,6-tetrahydropyridin-4-yl)-5-nitro-1H-indole,]

*1-(2'-Fluorophenyl)-3-(1-(2-(2-imidazolidinon-1-*yl)*ethyl)-1,2,3,6-tetrahydropyridin-4-*yl)-5-nitro-*1H*-indole, maleate. (Lu 24-024). M.p. 200°C.

[1-(4'-Fluorophenyl)-3-(1-pyrrolo-2-ethyl)-1,2,3,6-tetrahydropyridin-4-yl)-5-trifluoromethyl-1H-indole,

*1-(4'-Fluorophenyl)-3-(1-(2-(1-pyrrolyl)ethyl)-1,2,3,6-*tetrahydropyridin-*4-yl)-5-trifluoromethyl-1H-indole,* maleate. (Lu 23-172).

[1-(4'-Fluorophenyl)-3-(1-pyrrolo-2-aceto-(1-1,2,3,6-tetrahydropyridin-4-yl)-5-trifluoromethyl-1H-indole

*1-(4'-Fluorophenyl)-3(1-pyrrolyl)carbonylmethyl-1,2,3,6-tetrahydropyridin-4-yl-5-trifluoromethyl-1H-*indole (2.5 g) was refluxed with $LiAlH_4$ (1 g) in dry THF (50 ml) for 1.5h. After cooling $H_2O$/THF was added to destroy excess of $LiAlH_4$. The precipitate was filtered off and THF evaporated. The remaining oil was dissolved in 2-propanol and the title compound precipitated as a maleate. Yield: 1.3 g (42%). M.p. 194°-195° C.

In a corresponding manner were also prepared:

[1-(4'-Fluorophenyl)-3-(1-(2-methyl-1-imidazoloe-2-ethyl)-1,2,3,6-tetrahydropyridin-4-yl)-5-trifluoromethyl-1H-indole,]

*1-(4'-Fluorophenyl)-3(1-(2-(2-methylimidazol-1-yl)ethyl)-1,2,3,6-tetrahydropyridin-4-yl)-5-trifluoromethyl-1H-indole,* difumarate. (Lu 23-173). M.p. 189°-191° C.

[1-(4'-Fluorophenyl)-3-(1-(1-imidazole-2-ethyl-1,2,3,6-tetrahydropyridin-4-yl)-5-trifluoromethyl-1H-indole,]

*1-(4'-Fluorophenyl)-3-(2-2-(imidazol-1-*yl)*ethyl)-1,2,3,6-tetrahydropyridin-4-yl)-5-trifluoromethyl-1H-indole,* dimaleate. (Lu 24-002). M.p. 165°-167° C.

EXAMPLE 7

(method f)

[1-(4'-Fluorophenyl)-3-(4-methyl-piperazino-1-)-5-trifluoromethyl-1H-indole,]

*1-(4'-Fluorophenyl)-3-(4-*methyl-*1-piperazinyl)-5-*trifluoromethyl-*1H-indole,* dihydrochloride. (Lu 21-123).

[2-Carboxymethyl-1-(4'-fluorophenyl)-5-trifluoromethylindolin-3-on]

*2-Carboxymethyl-1-(4'-fluorophenyl)-5-trifluoromethylindolin-3-one* (15 g) and $MgCl_2 \cdot 6H_2O$ (30 g) in HMPA (100 ml) were heated under $N_2$ at 120°-140° C. for 1 h and finally at 150° C. for another ½ h. [1-Methylpiperazin] *1-*Methyl-piperazine (25 ml) was added and the mixture was refluxed under $N_2$ at an oil bath temperature of 200° C. for 16 h. The mixture was cooled and poured into 1 ltr. of $H_2O$ and extracted with ether 3×200 ml). The combined ether extracts were washed with 0.5 M HCl (3×300 ml). The acidic $H_2O$ phase was made alkaline and reextracted with ether (2×200 ml). The combined organic phase was dried ($MgSO_4$) and the ether evaporated. The remaining oil was dissolved in acetone and the title compound precipitated as a dihydrochloride. Yield: 6.7 g (35%). M.p. 245°-247° C.

In a corresponding manner the following 3-piperazinoindoles were prepared:

[1-(4'-Fluorophenyl)-3-(4-(2-hydroxyethyl)-1-piperazino-5-trifluoromethyl-1H-indole.]

*1-(4'-Fluorophenyl)-3-(4-(2-hydroxyethyl)-1-*piperazinyl)-*5-*trifluoromethyl-*1H-indole.* (Lu 21-152). M.p. 164° C.

[1-(4'-Fluorophenyl)-3-piperazino-5-trifluoromethyl-1H-indole.]

*1-(4'-*Fluorophenyl)-*3-(1-*piperazinyl-*5-trifluoromethyl-1H-indole.* (Lu 21-153). M.p. 168°-170° C.

[1-(4'-Fluorophenyl)-3-(4-isopropyl-piperazino-5-trifluoromethyl-1H-indole,[

*1-(4'-Fluorophenyl)-3-(4-isopropyl-1-piperazinyl-5-trifluoromethyl-1H-indole,* dihydrochloride. (Lu 23-016). M.p. 278°-280° C.

[5-Chloro-3-(4-methylpiperazino-1-phenyl-1H-indole.]

*5-Chloro-3-(4-methyl-1-piperazinyl)-1-phenyl-1H-indole.* (Lu 23-015). M.p. 174°-175° C. *Lu 23-011 (see Table 1).*

EXAMPLE 8

(method g)

1-(4'-Fluorophenyl)-5-methyl-3-(1-methyl-4-piperidyl)-1H-indole, hydrobromide. (Lu 21-037).

To 14 g of Mg turnings was added 4-chloro-1-methylpiperidine (35 g) in dry THF (500 ml). The mixture was refluxed for 1 hour and filtered under $N_2$ into an ice cooled solution of 1-(4'-fluorophenyl)-5-methylisatin (60 g) in dry THF (500 ml). The mixture was heated to reflux and poured into $H_2O$ (1 ltr.) saturated with $NH_4Cl$ and extracted with ether (2×300 ml). The combined organic phases were dried ($MgSO_4$), the ether evaporated yielding 48.5 g (58%) of 1-(4'-fluorophenyl-3-hydroxy-5-methyl-3-(1-methyl-4-piperidyl)indolin-2-on. M.p. 177°-179° C.//To a suspension of $LiAlH_4$(1 g) in dry THF (100 ml) was added 2.5 g of the above prepared indolin-2-on. The mixture was refluxed for 1 hour, excess of [$LiAlH_4$destroyed] *$LiAlH_4$ destroyed* by addition of $H_2O$ / THF, and filtered; and 2 M HCl (500 ml) was added to the filtrate and gently heated. The $H_2O$ phase was made alkaline and the product extracted with ether (2×300 ml). The combined ether phases were dried ($MgSO_4$) and the ether evaporated. The remaining oil was dissolved in acetone and 1-(4'- fluorophenyl)-5-methyl-3-(1-methyl-4-piperidyl) [indolin-2-on] *indolin-2-one* was precipitated an oxlate. Yield: 2.0 g (66%). M.p. 222° C. To a solution of [$B_2H_6$in] $B_2H_6$ in THF (100 ml) kept under $N_2$ at 0°C. was added 11.0 g of the oxalate salt prepared as above. The mixture was heated slowly to 50° C. and kept there for 2 hours. It was finally poured onto ice (1 ltr.) and extracted with ether (2×200 ml). The combined ether phases were dried ($MgSO_4$) and the ether evaporated. The remaining oil was dissolved in 2-propanol and the title compound precipitated as a hydrobromide salt. Yield: 3.7 g (36%). M.p. 254°-256° C.

EXAMPLE 9

5-Amino-1-(4'-fluorophenyl)-3-(1-methyl-1,2,3,6-tetrahydropyridin-4-yl)-1H-indole, fumarate. (Lu 23-149)

[1-(4'-Fluorophenyl)-3-(methyl-1,2,3,6-tetrahydropyridin-4yl)-5-nitro-1H-indole]

*1-(4'-Fluorophenyl)-3-(1-methyl-1,2,3,6*-tetrahydropyridin-*4*-yl)-*5-nitro-1*H-indole (Lu 22-135) (10 g) in 90% ethanol (150 ml) was heated to reflux and dil. HCl (2 ml) and Fe-powder (5 g) were added within 0.5 hour. Reflux was continued for another hour. The reaction mixture was filtered, cooled down and subsequently poured into 1 liter of [$NH_4Oh$] $NH_4OH$ and extracted with ethyl acetate (2×400 ml). The combined organic phases were dried ($MgSO_4$) and the solvent evaporated. The remaining oil [and] *was* purified by column chromatography on silica gel (eluted with ethyl acetate/methanol 1:1 containing 2% of triethylamine). The title compound was finally precipitated as a fumarate from ethanol/acetone (1:1). Yield 4.2 g (34%). M.p. 128°-134° C.

EXAMPLE 10

[1-(4'-Fluorophenyl)-3-(4-(2-(pyrrolidin-2-thion-1-yl)-ethyl-1-piperazino-5-trifluoromethyl-1H-indole]

*1-(4'-Fluorophenyl )-3-(4-(2-(pyrrolidin-2*-thion-*1*-yl)-*ethyl)-1-piperaziny)-5-trifluor methyl-1H*-indole (Lu 23-018).

The pyrrolidonyl indole derivative (Lu 22-133) (2.8 g) prepared in Example 4 and p-methoxyphenylthionophosphine sulfide dimer (2.0 g) (Lawesson reagent) were heated in HMPA (25 ml) at 110° C. for 1 hour. The reaction mixture was poured into $H_2O$ (500 ml) and $K_2CO_3$(10 g) added. The product was extracted with ether containing 10% of ethyl acetate (2×200 ml). The combined organic phases were dried ($MgSO_4$), the solvents evaporated and the resulting crystalline product was recrystallized from ethanol yielding 2.1 g (73%) of the title compound. M.p. 199°-201° C.

EXAMPLE 11

[3-(4-(1-Acetyloxyethyl)-1-piperazino-1-(4'-fluorophenyl)-5-trifluoromethyl-1H-indole.]

*3-(4-(2-(1-Acetyloxy)ethyl)-1-piperazinyl)-1-(4'-fluorophenyl)-5-trifluoromethyl-1H-indole.* (Lu 23-161).

[1-(4'Fluorophenyl-3-(4-(2-hydroxyethyl)-1-piperazinol)-5-trifluoromethyl-1H-indole]

*1-(4'-Fluorophenyl)-3-(4-(2*-hydroxyethyl)-*1*-piperazinyl)-*5-trifluoromethyl-1H-indole* (Lu 21-152) (5 g) was heated to reflux in acetone (50 ml). Acetylchloride (2 ml) was added slowly. Refluxing was continued for 1.5 h. The solvent was evaporated and the remaining oil was extracted with $CH_2Cl_2$(2×200 ml) from $NH_4OH$ at [Ph] *pH* 10. The combined organic phases were dried ($MgSO_4$) and the solvent evaporated. The title compound precipitated from ether. Yield: 3.7 g (72%). M.p. 129°-131° C.

In a corresponding manner the following esterified indole derivatives were prepared:

3-(4-(1-decanoyloxyethyl)-1-piperazino)-1-(4'-fluorophenyl)-5-trifluoromethyl-1H-indole. (Lu 23-162). M.p. 71°-73° C.

1-(4'-Fluorophenyl)-3-(4-(1-oleyloxyethyl)-1-piperazino)-5-trifluoromethyl-1H-indole, dihydrochloride. (Lu 23-163). M.p. 158°-162° C.

The compounds of Formula I were tested according to reliable and well recognized pharmacological tests as follows:

1. Methylphenidate antagonism

The inhibiting effect of test substances on the methylphenidate-induced gnawing in mice is determined as described by Pedersen and Christensen (1972).

The test substance is given i.p. in different doses, while methylphenidate is given s.c. in the dose 60 mg/kg, ½, 2 or 24 hours after injection of test substance. Per dose of the test substance is used 3×2 mice $\sigma$, 18-25 g). The results are given in fractions: 0/3, ⅓, ⅔ and 3/3, where 0,1,2 and 3 are the number of pairs, which [has] *have not been gnawing on receipt of the test substance.*

Ref:

Pedersen, V. and Christensen, A.V.; Acta pharmacol. et toxicol. 31, 488–496, 1972.

2. Catalepsy

Evaluation of catalepsy is made according to Arnt (1983). The rat is placed on a vertical wire mesh (mesh diameter 12 mm) and considered as cataleptic if it remains immobile for more than 15 seconds. The number of cataleptic rats in each dose group is determined every hour, 1–6 hours and 24 hours following peroral administration of test compound. The maximal numbers of cataleptic rats in each of at least 3 dose groups, each consisting of at least 4 rats, is recorded. These numbers are used for calculation of [$ED_{50}$values] $ED_{50}$ *values by log-probit analysis.*

Ref.:

Arnt, J.: European J. Pharmacol. 90, 47–55, 1983.

3. Quipazine inhibition

Quipazine and a number of other compounds, which increase [5-$HT_2$receptor] 5-$HT_2$ *receptor* activity in the CNS, induce a characteristic rapid shake (twitch) of the head. This response is inhibited by 5-$HT_2$ receptor antagonists (Vetulani et al. 1980, Arnt et al. 1984).

The test compound or saline is injected subcutaneously 2 hours before subcutaneous injection of quipazine hemimaleate (15 μmol/kg). At least 3 dose groups, each consisting of at least 4 rats, are used. The rats are individually placed in observation cages (12×25 cm) and the number of head twitches are counted 30–40 min after quipazine administration. Inhibition of head twitches is expressed in per cent of the number of head twitches in the control group. [ED 50] $ED_{50}$ values are calculated by log-probit analysis.

Ref.:

Vetulani, J., B.B. Beduarczyk, K. Reichenberg and A. Rokost: Neuropharmacology 19, 155–158, [1983].

Arnt, J., J. Hyttel and J.-J. Larsen: Acta pharmacol. et toxicol. 55, 363–372, 1984.

4. $^3$H-spiroperidol bindings

The affinity of compounds to dopamine (DA) D-2 receptors and serotomin$_2$(5-$HT_2$) receptors was determined by in vitro receptor binding technique. Binding of $^3$H-spiroperidol to DA D-2receptors in rat striatal membranes and to 5$HT_2$ receptors in rat cortical membranes was determined as described in detail by Arnt et al. (1984).

Ref.:

Arnt, J.,J. Hyttel and J.-J. Larsen: Acta pharmacol. et toxicol. 55, 363-372 1984.

TABLE 1

| Compound No. | MePh Antg. ED50(ip) (μmol/kg) | Pharmacology of Indoles: Catalep. ED50(po) (μmol/kg) 1-6 h | 24 h | Qvipaz. inh. ED50(sc) (μmol/kg) | $^3$H-Spiroperidol bindings: DA-2 receptors $IC_{50}/10^{-9}$ M | 5-$HT_2$ receptors $IC_{50}/10^{-9}$ M |
|---|---|---|---|---|---|---|
| Lu 20-089 | 0.18 | 0.43 | 6.5 | 0.12 | 0.34 | 1.8 |
| Lu 21-018 | 0.58 | 2.00 | >6.9 | 0.15 | 0.74 | 3.0 |
| Lu 21-037 | 2.10 | | | | | |
| Lu 21-046 | 48.1 | | | 0.23 | | |
| Lu 21-120 | 0.08 | 0.32 | 0.35 | 0.03 | 0.61 | 3.1 |
| Lu 21-123 | 0.09 | 0.08 | 0.62 | 0.035 | 1.7 | 6.7 |
| Lu 21-131 | 0.60 | 0.59 | 2.2 | | | |
| Lu 21-152 | 0.11 | 0.17 | 0.28 | 0.023 | 2.8 | 7.4 |
| Lu 21-153 | 2.0 | 7.1 | 16.0 | 0.37 | 3.7 | 6.7 |
| Lu 22-117 | 0.06 | 0.09* | >0.37* | 0.052 | 1.2 | 0.66 |
| Lu 22-133 | 0.82 | 0.66* | 1.7* | 0.15 | | 1.9 |
| Lu 22-134 | 1.7 | 2.7* | >2.7* | 2.5 | 5.3 | |
| Lu 22-135 | 0.10 | 0.078 | >0.89* | 0.009 | 1.1 | 1.9 |
| Lu 23-001 | 0.22 | 1.2 | 2.6 | 0.047 | 6.6 | 18 |
| Lu 23-011† | 0.12* | 0.55 | >1.8 | 0.041 | | 0.38 |
| Lu 23-015 | 8.8 | 12.0 | >15 | 0.062 | 12.0 | 3.9 |
| Lu 23-018 | 53.0 | 1.2 | 2.9 | | | |
| Lu 23-024 | 0.65 | 6.8* | >10* | | | 5.3 |
| Lu 23-075 | 19* | | | 0.18 | | |
| Lu 23-083 | 1.3* | 9.4 | >14 | 0.15 | 1.8 | |
| Lu 23-086 | >98* | | | 0.036 | 42 | 2.9 |
| Lu 23-133 | 18* | 11.0 | >11 | | 5.9 | |
| Lu 23-134 | 9.0* | 1.1 | >8.8 | | 2.8 | 15 |
| Lu 23-142 | 2.6* | | | | | 6.7 |
| Lu 23-143 | 72.0* | >18* | >18* | [4.5] >4.5 | | |
| Lu 23-146 | 0.73* | 1.0* | | | | |
| Lu 23-147 | >99* | | | | | |
| Lu 23-148 | >91* | | | | | |
| Lu 23-149 | 0.45* | | | | | |
| Lu 23-150 | 0.07* | 0.21 | | | 4.7 | 10 |
| Lu 23-155 | 3.8* | | | | | |
| Lu 23-156 | 0.07* | <0.19* | 1.1* | 0.03 | 19 | 15 |
| Lu 23-157 | 0.37* | 0.49* | 2.6* | 0.12 | | |
| Lu 23-158 | 2.9* | | | 0.11 | | |
| Lu 23-159 | 47* | | | | | |
| Lu 23-160 | 3.4* | 5.2* | [5.2*] | | 11 | 34 |
| Lu 23-161 | 0.05* | 0.09* | 0.18* | | | |
| Lu 23-162 | 1.7* | | | | | |
| Lu 23-163 | 1.1* | | | | | |
| Lu 23-167 | 2.7* | 2.7* | >11.0* | | | |
| Lu 23-171 | 0.11* | | | | | |
| Lu 23-172 | >70* | | | >0.55 | 31 | |
| Lu 23-173 | 0.77* | 1.8* | | >7.1 | 42 | 60 |
| Lu 23-174 | >72* | | | 0.49 | 20 | 6.6 |
| Lu 23-175 | 0.32* | 0.68* | | | 11 | 6.7 |
| Lu 24-001 | 2.6* | | | 0.19 | | 8.8 |
| Lu 24-002 | 0.45* | | | >0.45 | | |
| Lu 24-003 | 0.09* | | | | 6.0 | 14 |
| Lu 24-004 | 1.1* | | | | | |
| Lu 24-012 | >20* | | | | | |
| Lu 24-013 | >20* | | | | | |
| Lu 24-014 | >22* | | | | | |
| Lu 24-015 | 3.8* | | | | | |
| Lu 24-016 | >30* | | | | | |
| Lu 24-022 | | | | | | |
| Lu 24-024 | | | | | | |
| Clorpromazine | 23 | 70 | | 0.38 | 24 | 30 |
| Cis(Z)Flupentizol | 0.14 | 2.4 | 19 | 0.042 | 3.2 | 13 |
| Haloperidol | 0.11 | 1.0 | | 0.99 | 8.2 | 58 |
| Tefludazine | 0.06 | 0.61 | 0.9 | 0.06 | 19 | 8.6 |

*ED50 from sc administration

† The compound Lu 23-011 is 5-chloro-1-(4-fluorophenyl)-3-(4-methyl-1-piperazinyl)indole. (See Column 9).

$LD_{50}$ i.v. in mice was determined for Lu 21-152 and Lu 22-135 to be 147 μmol/kg and 276 μmol/kg respectively which indicates a comparatively low acute toxicity as compared with known neuroleptics such as chlorpromazine, cis(Z)-flupentixol and tefludazin having values between 120-180 μmol/kg.

The compounds of Formula I and the non-toxic acid addition salts thereof may be administered to animals such as dogs, cats, horses, sheeps or the like, including human beings, both orally and parenterally, and may be used for example in the form of tables, capsules, powders, syrups or in the form of the usual sterile solutions for injection. [-Results upon administration to human beings have been very gratifying.]

Most conveniently the compounds of Formula I are administered orally in unit dosage form such as tablets or capsules, each dosage unit containing the free amine or a non-toxic acid addition salt of one of the said compounds in an amount of from about 0.10 to about 100 mg, most preferably, however, from about 5 to 50 mg, calculated as the free amine, the total daily dosage usually ranging from about 1.0 to about 500 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

When the compound of Formula I is an ester, preferably a decanoic acid ester, palmitic acid ester or a behenic acid ester, the composition may advantageously be an oily solution for injection, and such solutions often have a very prolonged effect when compared with the corresponding unesterified compound.

Typical examples of formulas for composition containing [1-(4'fluorophenyl)-3-(4-(2-hydroxyethyl-1-piperazinyl)-5-trifluoromethylindole] 1-(4'-*fluorophenyl*)-3-(4-(2-*hydroxyethyl*)-188-*piperazinyl*)-5-*trifluoromethylindole* (called Lu 21-132 for short) as the active ingredient, are as follows:

| (1) Tablets containing 5 milligrams of Lu 21-152 calculated as the free base: | |
|---|---|
| Lu 21-152 | 5 mg |
| Lactose | 18 mg |
| Potato starch | 27 mg |
| Saccharose | 58 mg |
| Sorbitol | 3 mg |
| Talcum | 5 mg |
| [Gelatine] Gelatin | 2 mg |
| Povidone | 1 mg |
| Magnesium stearate | 0.5 mg |
| (2) Tablets containing 50 milligrams of Lu 21-152 calculated as the free base: | |
| Lu 21-152 | 50 mg |
| Lactose | 16 mg |
| Potato starch | 45 mg |
| Saccharose | 106 mg |
| Sorbitl | 6 mg |
| Talcum | 9 mg |
| [Gelatine] Gelatin | 2 mg |
| Povidone | 3 mg |
| Magnesium stearate | 0.6 mg |
| (3) Syrup containing per milliliter: | |
| Lu 21-152 | 10 mg |
| Sorbitol | 500 mg |
| Tragacanth | 7 mg |
| Glycerol | 50 mg |
| Methyl-paraben | 1 mg |
| Proyl-paraben | 0.1 mg |
| Ethanol | 0.005 ml |
| Water | ad 1 ml |
| (4) Solution for injection containing per milliliter: | |
| Lu 21-152 | 50 mg |
| Acetic acid | 17.9 mg |
| Sterile water | ad 1 ml |
| (5) Solution for injection containing per milliliter: | |
| Lu 21-152 | 10 mg |
| Sorbitol | 42.9 mg |
| Acetic acid | 0.63 mg |
| Sodium hydroxide | 22 mg |
| Sterile water | ad 1 ml |

Any other pharmaceutical tableting adjuvants may be used provided that they are compatible with the active ingredient, and additional compositions and dosage forms may be similar to those presently used for neuroleptics, such as [chlorpenthixol] *clopenthixol*, flupentixol or fluphenazine.

Also combinations of the compounds of Formula I as well as their non-toxic acid salts with other active ingredients, especially other neuroleptics, thymoleptics, tranquilizers, [analgetics] *analgesics* or the like, fall within the scope of the present invention.

As previously stated, when isolating the compounds of Formula I in the form of an acid addition salt the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethane-sulphonates, lactates, citrates, tartrates or bitartrates, pamoates and maleates of the amines of Formula I. Other acids are likewise suitable and may be employed if desired. For example: [fumaric] *fumaric*, benzoic, ascorbic, succinic, salicylic, bismethylenesalicylic, propionic, malic, malonic, mandelic, cannamic, citraconic, stearic, palmitic, itaconic, glycolic, benzenesulphonic, and sulphamic acids may also be employed as acid addition saltforming acids.

When is it desired to isolate a compound of the invention in the form of the free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalities of animals, including psychoses, by administering to a living animal body, including human beings, an adequate quantity of a compound of Formula I or a non-toxic acid addition salt thereof. An adequate quantity would be from about 0.001 mg to about 10 mg per kg of body weight in each unit dosage, and from about 0.003 milligrams to about 7 milligrams/kg of body weight per day.

It is to be understood that the invention is not limited to the exact details of operation or exact compound or compositions shown and described, as obvious modifications and equivalents will be apparent to one skilled in the art. and equivalents will be apparent to one skilled in the art.

I claim:

1. A compound selected from the group consisting of (a) an indole derivative of the following formula:

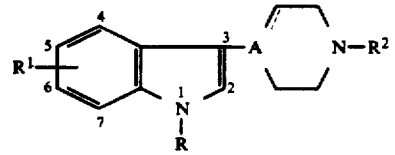

wherein R is selected from (*a*) phenyl, optionally substituted with [one substituent selected from] halogen [and trifluoromethyl] and (*b*) a hetero aromatic group selected from 2-thienyl, 3-thienyl, [2-furoyl, 3-furoyl, 2-thiazol, 2-oxazol, 2-imidazole, 2-pyridyl, 3-pyridy] *2-oxazolyl, 2-imidazolyl, 2-pyridyl* and 4-pyridyl;

$R^1$ is selected from hydrogen, halogen, lower alkyl, lower alkoxy, hydroxy, cyano, nitro, lower alkylthio, trifluoromethyl, lower alkylsulfonyl, amino, lower alkylamino and lower di-alkylamino;

"A" is selected from nitrogen and carbon, and the dotted line indicates—when A is carbon—an optional bond;

$R^2$ is selected from hydrogen, [cycloakyl] *cycloalkyl* of [$C_3$-$C_4$ ] $C_3$-$C_6$ ]inclusive] *inclusive,* lower alkyl and lower alkenyl, optionally substituted with one or two hydroxy groups, any hydroxy group present being optionally esterified with an aliphatic carboxylic acid having from two to twenty-four carbon atoms inclusive, and the group

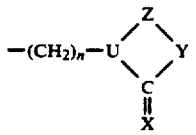

wherein "n" is an integer of 2–6;

X is selected from oxygen and sulfur, [C=X] >*C=X* may constitute the group [CH] —*CH* = when Y is selected from =N— and =CH—;

Y is selected from oxygen, sulfur, $CH_2$ and N-$R^3$, where $R^3$ is selected from [hydrogen and] *hydrogen,* lower alkyl, lower alkenyl and a cycloalkylmethyl group, said "cycloalkyl" having from three to six carbon atoms inclusive;

Z is selected from —$(CH_2)_m$—, "m" being selected from 2 and 3, [and —CH=CH and] —*CH=CH,* 1,2-phenylene optionally substituted with a group selected from halogen and trifluoromethyl, and —CO (or S) $CH_2$—;

U is selected from nitrogen and carbon, provided that when $R^1$ is *hydrogen,* chloro, *lower alkyl, methoxy or hydroxy,* A is nitrogen and $R^2$ is selected from [methyl] *lower alkyl* and [cyclohexyl,] *cycloalkyl of* $C_3$-$C_6$, R may not be phenyl; [and] *or*

(b) a pharmaceutically acceptable acid addition salt thereof.

2. An indole derivative of claim 1, wherein $R^1$ is selected from chlorine, fluorine, trifluoromethyl, methyl, nitro and amino in the 5-position, R is phenyl substituted with fluorine in the 4'- or 2'-position, [$R^2$is] $R^2$ is selected from methyl, 2-hydroxyethyl and 3-hydroxypropyl, and A is as defined in claim 1.

3. *An indole derivative of claim* [Claim] 1 *wherein the* compound *is* selected from [1-(4'-Fluorophenyl)-3-(4-(2-hydroxyethyl)-piperazino)-5-trifluoromethyl-1H-indole,] *1-(4'-Fluorophenyl)-3-(4-(2-hydroxyethyl)-1-piperazinyl-5-trifluoromethyl-1H*-indole, 1-(4'-Fluorophenyl)-5-nitro-3-(1-methyl-1,2,3,6-tetrahydropyridin-4-yl)-1H-indole, 5-Chloro-1-(4'-fluorophenyl)-3-(1-methyl-1,2,3,6-tetrahydropyridin-4-yl)-1H-indole, 1-(4'-Fluorophenyl)-3-(1-(2-hydroxyethyl)-1,2,3,6-tetrahydropyridin-4-yl)-5-nitro-1H-indole, 1(4'-Fluorophenyl)-3-(1-(2-hydroxyethyl)-1,2,3,6-tetrahydropyridin-4-yl)-5-trifluoromethyl-1H-indole, 5-Fluoro-1-(4'-fluorophenyl)-3-(1-(3-hydroxypropyl)-1,2,3,6-tetrahydropyridin-4-yl)-1H-indole, [and] *or* pharmaceutically acceptable acid addition salts thereof.

4. A neuroleptic or thymoleptic pharmaceutical composition suitable for use in the treatment of disorders amenable to such medication in unit dosage form comprising, as an active ingredient, a compound as defined in claim 1 in an amount effective for such purpose, together with one or more pharmaceutical diluents or carriers.

5. A pharmaceutical composition in unit dosage form, according to claim 4, wherein the active ingredient is present in an amount from 0.10 to 100 milligrams per unit dosage.

6. A pharmaceutical composition in unit dosage form, according to claim 4 wherein the active ingredient is a compound of claim 3.

7. A method for the treatment of disorders amenable to [neuroleptic or] thymoleptic medication comprising administering a [neuroleptic or] thymoleptically-effective amount in unit dosage form of a compound of claim 1, as an active ingredient, optionally together with one or more pharmaceutical diluents or carriers, to a warmblooded animal including a human being.

8. A method according to claim 7, wherein the active ingredient is present in an amount from 0.1 to about 100 mg per unit dosage.

9. A method according to claim 8, wherein the active ingredient is 1-(4'-fluorophenyl)-3-(4(2-hydroxyethyl)-1-piperazinyl)-5-trifluoromethyl-indole, or a pharmaceutically acceptable salt thereof.

* * * * *

UNITED STATES PATENT AND TRADEMARK OFFICE

CERTIFICATE OF CORRECTION

PATENT NO. : Re. 34,299

DATED : June 29, 1993

INVENTOR(S) : Jens K. Perregaard

It is certified that error appears in the above-indentified patent and that said Letters Patent is hereby corrected as shown below:

| | |
|---|---|
| Abstract, 3rd Paragraph, Line 7 | Delete *3-pyridyl* (second occurrence). |
| Abstract, 3rd Paragraph, Line 20 | Delete "<" and insert -->--; delete "=" (second occurrence) and insert a hyphen. |
| Abstract, 3rd Paragraph, Line 29 | Delete "A" and insert --"A"--. |
| Abstract, 3rd Paragraph, Line 50 | Delete "alky" and insert --alkyl--. |
| Column 1, Line 21 | After "phenyl", insert --]--. |

UNITED STATES PATENT AND TRADEMARK OFFICE

CERTIFICATE OF CORRECTION

PATENT NO. : Re. 34,299

DATED : September 13, 1991

INVENTOR(S) : Jens K. Perregaard

It is certified that error appears in the above-indentified patent and that said Letters Patent is hereby corrected as shown below:

| | |
|---|---|
| Column 1, Lines 22-23 | Remove the italics (should not be italicized). |
| Column 1, Line 24 | Delete "piperazineimdole" and insert --piperazineindole--. |
| Column 1, Line 42 | Delete "active" and insert --inactive--. |
| Column 6, Line 48 | Delete "105° C." and insert --105°-107° C.--. |
| Column 7, Line 18 | Italicize the word "imidazolidinon". |
| Column 7, Line 23 | Italicize the entire line. |
| Column 7, Lines 28-29 | Italicize both lines through the word "indole". |

UNITED STATES PATENT AND TRADEMARK OFFICE

CERTIFICATE OF CORRECTION

PATENT NO. : Re. 34,299

DATED : September 13, 1991

INVENTOR(S) : Jens K. Perregaard

It is certified that error appears in the above-indentified patent and that said Letters Patent is hereby corrected as shown below:

| | |
|---|---|
| Column 7, Line 51 | After "indole.", insert --]--. |
| Column 7, Line 52 | After " 3-( " insert -- 1- --. |
| Column 7, Lines 52-53 | Italicize both lines through the word "indole". |
| Column 8, Line 36 | Delete "1yl" and insert --1-yl--. |
| Column 8, Line 54 | After "-3-", insert -- (4- --. |
| Column 8, Line 59 | Italicize the entire line. |
| Column 9, Line 1 | After "(1-", insert -- (2- --. |

UNITED STATES PATENT AND TRADEMARK OFFICE

CERTIFICATE OF CORRECTION

PATENT NO. : Re. 34,299

DATED : September 13, 1991

INVENTOR(S) : Jens K. Perregaard

It is certified that error appears in the above-indentified patent and that said Letters Patent is hereby corrected as shown below:

| | |
|---|---|
| Column 9, Line 6 | After "3-", insert -- (1- --; after "(2" (first occurrence), insert a hyphen. |
| Column 9, Line 7 | Italicize the word "tetrahydropyridin". |
| Column 9, Line 13 | Italicize the word "nitro". |
| Column 9, Line 19 | Italicize the entire line. |
| Column 9, Line 25 | Italicize the word "trifluoromethyl". |
| Column 9, Line 32 | Italicize the entire line through the word "indole". |
| Column 9, Line 35 | After "indole", insert -- ] --. |

UNITED STATES PATENT AND TRADEMARK OFFICE

CERTIFICATE OF CORRECTION

PATENT NO. : Re. 34,299

DATED : September 13, 1991

INVENTOR(S) : Jens K. Perregaard

It is certified that error appears in the above-indentified patent and that said Letters Patent is hereby corrected as shown below:

| | |
|---|---|
| Column 9, Lines 36-37. | Italicize the word "tetrahydropyridin". |
| Column 9, Line 40 | After "indole", insert -- ] --. |
| Column 9, Line 41 | After "-3", insert -- -(1- --. |
| Column 9, Line 54 | After "-3", insert a hyphen. |
| Column 9, Line 60 | Delete "3-(2" and insert -- 3-(1-( --. |
| Column 10, Lines 1-2 | Italicize both lines through the word "dihydrochloride". |

UNITED STATES PATENT AND TRADEMARK OFFICE

CERTIFICATE OF CORRECTION

PATENT NO. : Re. 34,299

DATED : September 13, 1991

INVENTOR(S) : Jens K. Perregaard

It is certified that error appears in the above-indentified patent and that said Letters Patent is hereby corrected as shown below:

| | |
|---|---|
| Column 10, Line 10 | Italicize "Methyl-piperazine". |
| Column 10, Lines 26-27 | Italicize both lines through the word "indole". |
| Column 10, Line 31 | Italicize the entire line. |
| Column 10, Line 34 | Delete "[" and insert -- ] --. |
| Column 11, Line 2 | After "precipitated", insert --as--. |
| Column 11, Lines 20-21 | Italicize both lines through the word "indole". |
| Column 11, Line 39 | Italicize both "thion" and "yl". |

UNITED STATES PATENT AND TRADEMARK OFFICE

CERTIFICATE OF CORRECTION

PATENT NO. : Re. 34,299

DATED : September 13, 1991

INVENTOR(S) : Jens K. Perregaard

It is certified that error appears in the above-indentified patent and that said Letters Patent is hereby corrected as shown below:

| | |
|---|---|
| Column 11, Line 40 | Italicize the word "indole". Delete "*piperaziny)-5-trifluor methyl*" and insert --*piperazinyl)-5-trifluoro-methyl*--. |
| Column 11, Line 61 | Italicize the word "hydroxyethyl". |
| Column 12, Line 24 | Remove the italics (should not be italicized). |
| Column 12, Lines 38-39 | Remove the italics (should not be italicized). |
| Column 12, Line 60 | After "[1983]", insert --1980--. |

UNITED STATES PATENT AND TRADEMARK OFFICE

CERTIFICATE OF CORRECTION

PATENT NO. : Re. 34,299

DATED : September 13, 1991

INVENTOR(S) : Jens K. Perregaard

It is certified that error appears in the above-indentified patent and that said Letters Patent is hereby corrected as shown below:

Column 15, Line 23 Delete "*(2-hydroxyethyl)-188-piperazinyl*" and insert -- *(2-hydroxyethyl)-1-piperazinyl* --.

Column 17, Line 7 Delete "]inclusive]" and insert -- [inclusive] --.

Column 18, Line 7 Italicize the word "indole".

Column 18, Line 45 After "-3-(4", insert a hyphen.

Signed and Sealed this

Third Day of May, 1994

*Attest:*

*Attesting Officer*

BRUCE LEHMAN

*Commissioner of Patents and Trademarks*